(12) United States Patent
Wang et al.

(10) Patent No.: US 8,895,735 B2
(45) Date of Patent: Nov. 25, 2014

(54) PREPARATION PROCESS OF (6R)-TETRAHYDROBIOPTERIN HYDROCHLORIDE

(75) Inventors: Zhen Wang, Sichuan (CN); Dongbing Zhao, Sichuan (CN); Weida Wang, Sichuan (CN); Jingbo Lan, Sichuan (CN); Jinsong You, Sichuan (CN)

(73) Assignee: Innopharmax, Inc., Taipei (TW)

( * ) Notice: Subject to any disclaimer, the term of this patent is extended or adjusted under 35 U.S.C. 154(b) by 0 days.

(21) Appl. No.: 13/879,285

(22) PCT Filed: Nov. 15, 2010

(86) PCT No.: PCT/CN2010/001836
§ 371 (c)(1),
(2), (4) Date: Apr. 12, 2013

(87) PCT Pub. No.: WO2012/048451
PCT Pub. Date: Apr. 19, 2012

(65) Prior Publication Data
US 2013/0197222 A1    Aug. 1, 2013

(30) Foreign Application Priority Data

Oct. 13, 2010    (CN) .......................... 2010 1 0505386

(51) Int. Cl.
*C07D 487/04*    (2006.01)
(52) U.S. Cl.
USPC ........................................................ 544/257

(58) Field of Classification Search
USPC ........................................................ 544/257
IPC ...................................................... C07D 487/04
See application file for complete search history.

(56) References Cited

U.S. PATENT DOCUMENTS

| | | |
|---|---|---|
| 4,595,752 A | 6/1986 | Azuma et al. |
| 4,713,454 A | 12/1987 | Sakai et al. |

FOREIGN PATENT DOCUMENTS

| | | | |
|---|---|---|---|
| JP | 60-204786 A | 10/1985 | |
| WO | WO 2009/088979 A | 7/2009 | |
| WO | WO 2009/088979 A1 * | 7/2009 | ............ C07D 487/04 |

OTHER PUBLICATIONS

International Search Report for PCT/CN2010/001836 mailed Jul. 21, 2011.

* cited by examiner

*Primary Examiner* — Paul V. Ward
(74) *Attorney, Agent, or Firm* — Birch, Stewart, Kolasch & Birch, LLP

(57) ABSTRACT

A preparation process of (6R)-tetrahydrobiopterin hydrochloride is provided, which comprises hydrogenating L-biopterin in the presence of a catalyst of Pt group metal in the basic substrate containing solvent, potassium hydroxide and potassium dihydrogen phosphate to obtain (6R)-tetrahydrobiopterin hydrochloride, wherein the pH value of the basic substrate is controlled by potassium hydroxide and potassium dihydrogen phosphate in the range of about 10 to about 13.

8 Claims, No Drawings

PREPARATION PROCESS OF (6R)-TETRAHYDROBIOPTERIN HYDROCHLORIDE

FIELD OF THE INVENTION

The present invention relates to a preparation process of (6R)-tetrahydrobiopterin hydrochloride.

BACKGROUND OF THE INVENTION (6R)-tetrahydrobiopterin (abbreviated as BH4), which belongs to the naturally-occurring pterin family, is a coenzyme produced by organisms per se. Pterins exist in organisms in both oxidized and reduced forms, but only the reduced form, (6R)-5,6,7,8-tetrahydrobiopterin, is biologically active, which is a coenzyme of phenylalanine hydroxylase. Lack of BH4 not only results in hyperphenylalaninemia but also affects the formation of various neurotransmitters so that the patient develops a series of symptoms of the nervous system that are different from those of a phenylketonuria patient, such as convulsions and paralysis.

The preparation of (6R)-tetrahydrobiopterin usually involves hydrogenation of L-biopterin (abbreviated as BH2) to obtain a mixture of R and S diastereomers, followed by multiple crystallization to obtain the desired product. US 2006/0142573 provides a method for preparing L-biopterin in a large industrial scale. U.S. Pat. No. 4,713,454 discloses a method for preparing (6R)-tetrahydrobiopterin by high-pressure hydrogenation of L-biopterin in the presence of a platinum-based catalyst, under the condition that the reaction substrate is controlled to be basic by use of an organic alkali (such as amines including primary, secondary, tertiary, and quaternary amines). It is specially emphasized in that patent that use of an inorganic alkali to control the pH value will reduce the R/S value (asymmetric ratio) of the products.

There is still a need in this art to improve the current preparation of (6R)-tetrahydrobiopterin, particularly to increase the easiness of operation in order to reduce production cost and facilitate industrial-scale production.

BRIEF SUMMARY OF THE INVENTION

The present invention for the first time provides a technical means of using potassium hydroxide and potassium dihydrogen phosphate to adjust the pH value of the reaction substrate in the hydrogenation of L-biopterin to prepare (6R)-tetrahydrobiopterin hydrochloride. The process of the present invention uses inorganic alkalis, i.e. potassium hydroxide and potassium dihydrogen phosphate, which provide the advantage of easy removal so as to simplify the operation procedures. It is also unexpectedly discovered that the process of the present invention permits a dramatic reduction of the solvent volume while maintaining the same product percent yield, and thus provides the effect of stabilizing the product percent yield so as to increase the unit production efficiency in a fixed-volume production tank and increase the easiness of operation, thereby facilitating the preparation of (6R)-tetrahydrobiopterin in a large industrial scale.

Therefore, in one aspect, the present invention provides a preparation process of (6R)-tetrahydrobiopterin hydrochloride, comprising hydrogenation of L-biopterin in the presence of a catalyst of a Pt group metal in a basic substrate containing a solvent, potassium hydroxide, and potassium dihydrogen phosphate to obtain (6R)-tetrahydrobiopterin hydrochloride, wherein the basic substrate is of a pH value, which is controlled by potassium hydroxide and potassium dihydrogen phosphate, in the range of about 10 to about 13.

In particular, in the process of the present invention, the ratio of L-biopterin to the solvent is in the range of about 1:10 to about 1:1000 (w/v), more specifically in the range of about 1:30 to about 1:100 (w/v). It is unexpected that the process of the present invention maintains substantially the same percent yield of (6R)-tetrahydrobiopterin hydrochloride even though the ratio of L-biopterin to the solvent varies widely, and thus provides the effect of stabilizing the product percent yield and thereby increases the unit production efficiency.

Preferably, the process of the present invention further comprises the steps of removing the catalyst, acidification, removing the solvent, and/or re-crystallization.

The details of one or more embodiments of the invention are set forth in the descriptions below. Other features of the present invention will be apparent from the following detailed description of several embodiments, and also from the appending drawings and claims.

It is believed that without further explanation, persons skilled in the art can still apply the present invention to its widest scope based on the descriptions herein. Therefore, the descriptions below should be treated as merely explanations but not restrictions to the scope of the present invention in any way.

DETAILED DESCRIPTION OF THE INVENTION

Unless defined otherwise herein, all scientific and technical terms related to the present invention have the same meanings as is commonly understood by one of skill in the art to which this invention belongs. As described herein, unless defined otherwise, the following terms have the meanings belonging thereto.

Unless required herein, a single noun shall include the meaning of a plural noun, while a plural noun shall include the meaning of a single noun. As used herein, the articles "a" and "an" refer to one or more than one (i.e., at least one) of the grammatical object of the article. By way of example, "an element" means one element or more than one element.

The process of the present invention is for preparing (6R)-tetrahydrobiopterin hydrochloride, comprising hydrogenation of L-biopterin in the presence of a catalyst of a Pt group metal in a basic substrate containing a solvent, potassium hydroxide, and potassium dihydrogen phosphate to obtain (6R)-tetrahydrobiopterin hydrochloride, wherein the basic substrate has a pH value, which is controlled by potassium hydroxide and potassium dihydrogen phosphate, in the range of about 10 to about 13.

The preparation process of the present invention can be illustrated by the following equation:

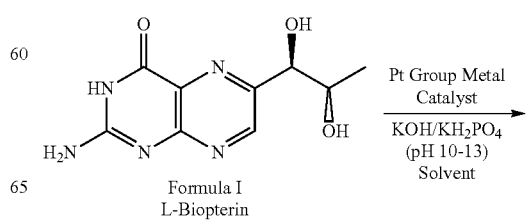

Formula I
L-Biopterin

-continued

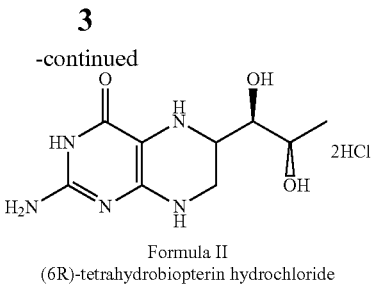

Formula II
(6R)-tetrahydrobiopterin hydrochloride

The hydrogenation preformed according to the present invention refers to the chemical reaction of addition of hydrogen gas to molecules with a double bond or multiple bond so that L-biopterin is hydrogenized to form (6R)-tetrahydrobiopterin.

The hydrogenation in the present invention is performed in a basic substrate with a pH value controlled to be about 10 to about 13 by potassium hydroxide and potassium dihydrogen phosphate, preferably controlled to be about 11 to about 12. Generally speaking, an organic alkali is an organic compound comprising an amine group in the molecule, such as amine compounds. In comparison, the present invention uses potassium hydroxide and potassium dihydrogen phosphate, which comprise no amine group and belong to inorganic alkalis.

The catalyst of a Pt group metal used in the process of the present invention can be any that is well known in the art, including but not limited to platinum black, platinum dioxide, platinum/carbon, or platinum/alumina, preferably platinum black or platinum dioxide. In the process of the present invention, the catalyst of a Pt group metal can be recycled and repeatedly used for multiple times, while the recycled catalyst would not reduce the production rate of hydrogenation products.

The hydrogenation in the present invention can be performed under a hydrogen pressure of about 1 to about 10 MPa, preferably about 1 to about 6 MPa, most preferably about 2 to about 4 MPa; the reaction temperature is about 0 to about 40° C., preferably about 10 to about 30° C.; the reaction time is about 20 to about 50 hours, preferably about 25 to about 40 hours.

The solvent for performing the hydrogenation of the present invention can be any that is well known in the art, including but not limited to water, alcohols, or combinations thereof; preferably water. For related literature, see U.S. Pat. No. 4,649,197.

According to the process of the present invention, those skilled in the art of the present invention may adjust the ratios of the catalyst of a Pt group metal, L-biopterin, and the solvent for performing the hydrogenation based on their own knowledge and/or requirements. The ratio of the catalyst of a Pt group metal to L-biopterin in weight is usually about 1% to about 30%, preferably about 10% to about 20%. The ratio (w:v) of the catalyst of a Pt group metal to the solvent is about 1:100 to about 1:2,000; preferably about 1:200 to about 1:1,000; most preferably about 1:300 to about 1:500. For related literature, see U.S. Pat. No. 4,595,752.

Specifically, according to the process of the present invention, the ratio of L-biopterin to the solvent for performing the hydrogenation is in the range of about 1:10 to about 1:1,000 (w/v), more specifically in the range of about 1:30 to about 1:100 (w/v). It is unexpected that the process of the present invention maintains substantially the same percent yield of (6R)-tetrahydrobiopterin hydrochloride even though the ratios in the range vary widely; that is, when the percent yields are compared with each other, their difference is no more than 5%, preferably no more than 3%. Therefore, the process of the present invention can be used to stabilize the product percent yield and thereby increases the unit production efficiency in a fixed-volume production tank and increases the easiness of operation to facilitate the preparation of (6R)-tetrahydrobiopterin in a large industrial scale.

The process of the present invention may further comprise the steps of removing the catalyst, acidification, removing the solvent, and/or re-crystallization.

In the process of the present invention, the catalyst in the hydrogenation may be removed by any known method, including but not limited to filtration such as normal-pressure filtration or reduced-pressure filtration, or centrifugal separation. For related literature, see U.S. Pat. No. 4,649,197.

Following the removal of the catalyst, acidification may be performed by adding an inorganic acid or an organic acid, wherein said inorganic acid may be, but is not limited to, hydrochloric acid or sulfuric acid, and said organic acid may be, but is not limited to, fumaric acid or tartaric acid. The pH value of the product from acidification with an organic acid is about 0 to about 6, preferably about 2 to about 5. The pH value of the product from acidification with an inorganic acid is about 0 to about 3, preferably about 1.

In addition, in the process of the present invention, the solvent may be removed by any known method, including but not limited to normal-pressure distillation or reduced-pressure distillation performed under a raised temperature or without a raised temperature.

Afterwards, the product may further be dissolved in a solvent, including but not limited to an alcohol, an alcohol aqueous solution, or a mixture of an acid aqueous solution and an alcohol, wherein the alcohol is preferably methanol, ethanol, or isopropanol; the acid aqueous solution is preferably made from hydrochloric acid, sulfuric acid, tartaric acid, or fumaric acid. The mixing ratio in volume of water to the alcohol in the alcohol aqueous solutions is about 1:10 to about 1:40, preferably about 1:20 to about 1:30. The mixing ratio in volume of the acid aqueous solution to the alcohol is about 1:10 to about 1:40, wherein the mixing ratio in volume of water to the acid in the acid aqueous solution is about 1:0.02 to about 1:1.

According to the process of the present invention, the product as prepared can be optionally further recrystallized for at least once to obtain (6R)-tetrahydrobiopterin hydrochloride of a high purity.

According to the present invention, the so-called "(6R)-tetrahydrobiopterin hydrochloride of a high purity" refers to (6R)-tetrahydrobiopterin hydrochloride with an enantiomeric excess (e.e.) percentage of more than about 99%, preferably more than about 99.5%. The enantiomeric excess percentage can be calculated using the following equation:

$$\frac{[R]-[S]}{[R]+[S]} \times 100\%$$

wherein [R] is the amount of the major enantiomeric product, and [S] is the amount of the minor enantiomeric product.

The re-crystallization in the present invention may be performed with the choice of a single solvent or a mixed solvent. The mixed solvent is generally composed of two solvents which are able to dissolve in each other in any ratio, wherein one solvent provides better solubility for the product, called good solvent, while the other solvent provides little solubility for the product, called poor solvent. During operation, the substance to be crystallized is first dissolved in the good solvent, and then the poor solvent is added in drops. The resulted mixture is left to cool for the crystal to form. For related literature, see US 2006/0035900.

The good solvent used to perform re-crystallization includes but is not limited to water, inorganic acids, organic acids, or mixtures thereof, wherein said inorganic acid may be, but is not limited to, hydrochloric acid or sulfuric acid, and said organic acid may be but is not limited to fumaric acid or tartaric acid. According to the present invention, the good solvent is preferably water, hydrochloric acid, or mixtures thereof. For related literature, see US 2006/0035900.

The poor solvent used to perform re-crystallization includes but is not limited to alcohols or ethers, wherein said alcohol may be but is not limited to methanol, ethanol, or isopropanol, and said ether may be but is not limited to tetrahydrofuran or 1,4-dioxane. According to the present invention, the poor solvent is preferably methanol, ethanol, or tetrahydrofuran. For related literature, see US 2006/0035900 and Chemistry Letters (1984) 735-738.

In the process of the present invention, the conditions for multiple re-crystallizations may be the same or different. In a preferred embodiment of the present invention, re-crystallization was performed twice, wherein the ratio of the good solvent to the (6R)-tetrahydrobiopterin hydrochloride product to be re-crystallized is about 1:1 to about 20:1 (v:w), preferably about 3:1 to about 10:1; in the first re-crystallization the ratio in volume of the good solvent to the poor solvent is about 1:1 to about 1:10, preferably about 1:1 to about 1:3; in the second re-crystallization the ratio in volume of the good solvent to the poor solvent is about 10:1 to about 10:20, preferably about 10:5 to about 10:15. When performing the first and second re-crystallizations, all operation conditions are identical except for the vastly different ratios of the good solvent to the poor solvent.

A certain amount of (6R)-tetrahydrobiopterin hydrochloride crystal may be added as a seed when performing re-crystallization. Said seed may be any (6R)-tetrahydrobiopterin hydrochloride crystal with an enantiomeric excess percentage of more than 99%.

In the process of the present invention the pH value of the reaction substrate is controlled by use of potassium hydroxide and potassium dihydrogen phosphate, which may be removed in the form of inorganic salts by simple post-treatments so as to increase the safety of (6R)-tetrahydrobiopterin hydrochloride in medicinal usage. Also, the catalyst of a Pt group metal in the process of the present invention may be easily recycled for repeated uses so as to reduce production costs. Furthermore, the process of the present invention permits widely varying ratios of L-biopterin to the solvent while maintaining the same product percent yield, and thus provides the effect of stabilizing the product percent yield so as to increase the unit production efficiency in a fixed-volume production tank and increase the easiness of operation, thereby facilitating the preparation of (6R)-tetrahydrobiopterin in a large industrial scale.

The present invention is further illustrated by the following examples, which are provided for the purpose of demonstration rather than limitation.

EXAMPLES

Example 1

Platinum dioxide (0.05 g) was added to 50 mL water and then 0.5 g L-biopterin was added with stirring. The pH value of the mixture was adjusted to 11.5 with potassium hydroxide and potassium dihydrogen phosphate, and the mixture was moved into an autoclave which was then filled with 4.0 MPa hydrogen gas. After reaction for 14° C. for 50 hours, the catalyst was removed by filtration and the pH value of the reaction mixture was adjusted to 1 with concentrated hydrochloric acid. Water in the reaction mixture was removed by reduced-pressure distillation to obtain a solid product with a ratio of (6R):(6S)=5.1:1 by HPLC analysis. Ethanol (20 mL) was added to dissolve the product and insoluble inorganic salts was removed by filtration. Solvent was removed from the filtrate under reduced pressure, and 2.5 mL 3M hydrochloric acid was added to dissolve the product. Anhydrous ethanol (5 mL) was added in drops and seeds were planted. The solution was placed under 0° C. to allow crystals to form and was then suction-filtered. The obtained white solid was dissolved in 1.5 mL 3M hydrochloric acid and 1.5 mL anhydrous ethanol was slowly added in drops to the solution, which was then placed under 0° C. for 6 hours to allow crystals to form slowly and was then suction-filtered and dried to obtained 0.27 g of white crystals of (6R)-tetrahydrobiopterin hydrochloride with purity>99.5%, e.e. value>99.5%, and a percent yield of 41%.

Example 2

Platinum dioxide (1 g) was added to 1,000 mL water and then 10 g L-biopterin was added with stirring. The pH value of the mixture was adjusted to 11.5 with potassium hydroxide and potassium dihydrogen phosphate, and the mixture was moved into an autoclave which was then filled with 4.0 MPa hydrogen gas. After reaction for 14° C. for 50 hours, the catalyst was removed by filtration and the pH value of the reaction mixture was adjusted to 1 with concentrated hydrochloric acid. Water in the reaction mixture was removed by reduced-pressure distillation to obtain a solid product with a ratio of (6R):(6S)=4.2:1 by HPLC analysis. Ethanol (400 mL) was added to dissolve the product and insoluble inorganic salts was removed by filtration. Solvent was removed from the filtrate under reduced pressure, and 80 mL 3M hydrochloric acid was added to dissolve the product. Anhydrous ethanol (160 mL) was added in drops and seeds were planted. The solution was placed under 4° C. to allow crystals to form and was then suction-filtered. The obtained white solid was dissolved in 50 mL 3M hydrochloric acid and 40 mL anhydrous ethanol was slowly added in drops to the solution, which was then placed under 4° C. for 6 hours to allow crystals to form slowly and was then suction-filtered and dried to obtained 3.96 g of white crystals of (6R)-tetrahydrobiopterin hydrochloride with purity>99.8%, e.e. value>99.8%, and a percent yield of 30%.

Example 3

Platinum dioxide (0.12 g), which has been used once, was added to 100 mL water and then 1.0 g L-biopterin was added with stirring. The pH value of the mixture was adjusted to 11.5 with potassium hydroxide and potassium dihydrogen phosphate, and the mixture was moved into an autoclave which was then filled with 4.0 MPa hydrogen gas. After reaction for 14° C. for 50 hours, the catalyst was removed by filtration and the pH value of the reaction mixture was adjusted to 1 with concentrated hydrochloric acid. Water in the reaction mixture was removed by reduced-pressure distillation to obtain a solid product with a ratio of (6R):(6S)=4.5:1 by HPLC analysis. Ethanol (400 mL) was added to dissolve the product and insoluble inorganic salts was removed by filtration. Solvent was removed from the filtrate under reduced pressure, and 6 mL 3M hydrochloric acid was added to dissolve the product. Anhydrous ethanol (12 mL)

was added in drops and the solution was placed under 4° C. to allow crystals to form and was then suction-filtered. The obtained white solid was dissolved in 4 mL 3M hydrochloric acid and 3 mL anhydrous ethanol was slowly added in drops to the solution, which was then placed under 4° C. for 6 hours to allow crystals to form slowly and was then suction-filtered and dried to obtained 0.45 g of white crystals of (6R)-tetrahydrobiopterin hydrochloride with purity>99.8%, e.e. value>99.8%, and a percent yield of 34%.

Example 4

Platinum dioxide (0.06 g), which has been used twice, was added to 50 mL water and then 0.5 g L-biopterin was added with stirring. The pH value of the mixture was adjusted to 11.5 with potassium hydroxide and potassium dihydrogen phosphate, and the mixture was moved into an autoclave which was then filled with 4.0 MPa hydrogen gas. After reaction for 14° C. for 50 hours, the catalyst was removed by filtration and the pH value of the reaction mixture was adjusted to 1 with concentrated hydrochloric acid. Water in the reaction mixture was removed by reduced-pressure distillation to obtain a solid product with a ratio of (6R):(6S) =4.5:1 by HPLC analysis. Ethanol (400 mL) was added to dissolve the product and insoluble inorganic salts was removed by filtration. Solvent was removed from the filtrate under reduced pressure, and 2.5 mL 3M hydrochloric acid was added to dissolve the product. Anhydrous ethanol (5 mL) was added in drops and the solution was placed under 4° C. to allow crystals to form and was then suction-filtered. The obtained white solid was dissolved in 1.5 mL 3M hydrochloric acid and 1 mL anhydrous ethanol was slowly added in drops to the solution, which was then placed under 4° C. for 6 hours to allow crystals to form slowly and was then suction-filtered and dried to obtained 0.23 g of white crystals of (6R)-tetrahydrobiopterin hydrochloride with purity>99.5%, e.e. value>99.5%, and a percent yield of 35%.

Example 5

Platinum dioxide (0.1 g) was added to 30 to 100 mL of water (as shown in Table 1) and then 1 g L-biopterin was added with stirring, and the pH value of the mixture was adjusted to 11.4 by adding potassium hydroxide and potassium dihydrogen phosphate. The mixture was placed into an autoclave and allowed to react for 50 hours under a hydrogen pressure of 4.0 MPa and 14° C. After the reaction, the catalyst was removed from the solution by filtration and the pH value of the filtrate was adjusted to 1 by adding concentrated hydrochloric acid. The filtrate then underwent reduced-pressure distillation in order to remove water to obtain a solid. The obtained solid was analyzed by HPLC for its 6R:6S reaction ratio as described in previous examples, and was re-crystallized via the same steps. The percent yield for pure products was calculated. Table 1 shows relevant reaction ratios and the pure product percent yield.

TABLE 1

| Solvent Amount (1 g BH$_2$) | Hydrogen Gas Transformation Ratio | 6R:6S | Pure Product Percent Yield | Temperature and Time |
| --- | --- | --- | --- | --- |
| 100 mL | >98% | 4.5:1 | 32% | 14° C., 50 hrs |
| 80 mL | >98% | 4.3:1 | 31% | 14° C., 50 hrs |
| 50 mL | >98% | 4.1:1 | 29% | 14° C., 50 hrs |
| 40 mL | >98% | 4.2:1 | 30% | 14° C., 50 hrs |
| 30 mL | >98% | 4.2:1 | 30% | 14° C., 50 hrs |
| 30 mL | >98% | 4.4:1 | 31% | 10° C., 36 hrs |

As shown in Table 1, according to the process of the present invention, using the same amount (1 g) of L-biopterin can maintain an almost identical percent yield (29-32%) for (6R)-tetrahydrobiopterin hydrochloride even when the solvent volume changes in the range of 30 to 100 mL. Therefore, the process of the present invention provides the effect of stabilizing the product percent yield so as to increase the unit production efficiency in a fixed-volume production tank and increase the easiness of operation, thereby facilitating the preparation of (6R)-tetrahydrobiopterin in a large industrial scale.

Those skilled in the art may combine all the characteristics disclosed in this specification by any combination. Each and every characteristic disclosed in this specification may be replaced by another characteristic used for identical, functionally equivalent, or similar objectives. Therefore, unless otherwise described, each of the disclosed characteristics is merely a series of common examples that are functionally equivalent or characteristically similar. Based on the above descriptions, those skilled in the art may make various changes and modifications to the present invention to accommodate various uses and conditions while not deviating from the spirit and scope thereof. Therefore, the present invention is not limited to the particular embodiments described herein, but comprises those described embodiments and all modifications within the scope of the appended claims.

What is claimed is:

1. A preparation process of (6R)-tetrahydrobiopterin hydrochloride, comprising
   hydrogenation of L-biopterin in the presence of a catalyst of a Pt group metal in a basic substrate containing a solvent, potassium hydroxide, and potassium dihydrogen phosphate to directly obtain (6R)-tetrahydrobiopterin hydrochloride, wherein the basic substrate is of a pH value, which is controlled by potassium hydroxide and potassium dihydrogen phosphate, in the range of about 10 to about 13.

2. The process according to claim 1, wherein the solvent is selected from the group consisting of water, alcohols, and combinations thereof.

3. The process according to claim 1, wherein the hydrogenation is performed under a hydrogen pressure of about 1 to about 10 MPa.

4. The process according to claim 1, wherein the hydrogenation is performed at about 0 to about 40° C.

5. The process according to claim 1, wherein the hydrogenation is performed for about 20 to about 50 hours.

6. The process according to claim 1, wherein L-biopterin and the solvent are present in a ratio ranging from about 1:10 to about 1:1000 (w/v).

7. The process according to claim 1, wherein L-biopterin and the solvent are present in a ratio ranging from about 1:30 to about 1:100 (w/v).

8. The process according to claim 1, which stabilizes percent yield of (6R)-tetrahydrobiopterin hydrochloride and thus increases unit production rate thereof.

* * * * *